United States Patent [19]
Baskas

[11] Patent Number: 5,161,970
[45] Date of Patent: Nov. 10, 1992

[54] DENTAL SAFE-HANDLING TOOL HOLDER

[75] Inventor: Morris J. Baskas, Bronxville, N.Y.

[73] Assignee: Unique Barrier Products Inc., New Rochelle, N.Y.

[21] Appl. No.: 629,243

[22] Filed: Dec. 18, 1990

Related U.S. Application Data

[63] Continuation-in-part of Ser. No. 520,733, May 9, 1990, Pat. No. 4,995,870, and a continuation-in-part of Ser. No. 595,238, Oct. 10, 1990, Pat. No. 5,035,703.

[51] Int. Cl.⁵ ............................................. A61G 15/00
[52] U.S. Cl. ........................................ 433/77; 433/79
[58] Field of Search ............................ 433/77, 79, 28; 604/110

[56] References Cited

U.S. PATENT DOCUMENTS

| | | | |
|---|---|---|---|
| 4,206,546 | 6/1980 | Runnells et al. | 433/79 |
| 4,330,281 | 5/1982 | Hayashi | 433/79 |
| 4,341,312 | 7/1982 | Scholer | 433/77 |
| 4,648,839 | 3/1987 | Timerdahl et al. | 433/77 |
| 4,880,381 | 11/1989 | Nieusma, Jr. | 433/28 |

Primary Examiner—Cary E. O'Connor

[57] ABSTRACT

A tool holder for mounting on the instrument panel in a dentist's office contains a grooved surface for receiving one or more syringe or scalpel or other implement holders. These holders have hexagonal bases for mounting in one of several different positions. A novel syringe holder employs a tapered threaded member for gripping the protective cover on the needle so that the cover can serve as the syringe holder.

13 Claims, 3 Drawing Sheets

DENTAL SAFE-HANDLING TOOL HOLDER

BACKGROUND OF INVENTION

This application is a continuation-in-part of my two earlier applications, Ser. Nos. 520,733 filed May 9, 1990 now U.S. Pat. No. 4,995,870 and 595,238 filed Oct. 10, 1990 now U.S. Pat. No. 5,035,703

RELATED APPLICATIONS

U.S. application, Ser. No. 520,733, filed May 9, 1990, entitled "DISPOSABLE SYRINGE WITH RETRACTABLE NEEDLE", now U.S. Pat. No. 4,995,870.

U.S. application, Ser. No. 595,238, filed Oct. 10, 1990, entitled "DISPOSABLE SYRINGE NEEDLE AND SCALPEL HOLDER", now U.S. Pat. No. 5,035,703.

This invention relates to safe handling of tools used by a dentist, and in particular to holders for scalpels and syringes and other tools and implements used by a dentist in his normal practice.

The referenced related applications Ser. Nos. 520,733 and 595,238, whose contents are hereby incorporated by reference, described devices for holding and handling syringes and scalpels in such manner that the disposable puncturing or cutting parts cannot be touched after use by the dental practitioner or his assistant.

These applications contemplated a special stand mounted on a cabinet or other convenient work surface in the treatment room.

SUMMARY OF INVENTION

It is an object of the invention to provide at a more convenient location means for supporting dental tool holders, preferably of the general type disclosed in my prior applications for safe handling of syringes and scalpel blades.

Another object of the invention is an improved holder for safe handling of a dental syringe.

According to one aspect of the invention, a mounting support device is provided that is constructed to mount on the dentist's instrument panel in his treatment room. The device is constructed to support a grooved member configured to receive one or more tool holders. Preferably the tool holders each have multi-sided mounting bases so that they can be supported on the grooved member in several different positions most convenient to the user.

In accordance with a further feature of this aspect of the invention, the grooved member is constructed to support a cup holder. The cup can be conveniently used to dispose of used dressings or implements.

In accordance with another aspect of the invention, a novel syringe holder is provided with an opening leading to a tapered threaded member mounted internally of the holder. The tapered threaded member is configured to receive a variety of sizes of standard syringe needle protective covers or sleeves which upon rotation can be temporarily locked to the tapered threaded member. This makes it very easy to detach the syringe from its sleeve, use the syringe, return it to and reattach it to its sleeve, and then by reverse rotation remove the syringe with its attached sleeve for safe disposal of the used needle.

The various features of novelty which characterize the invention are pointed out with particularity in the claims annexed to and forming a part of this disclosure.

For a better understanding of the invention, its operating advantages and specific objects attained by its use, reference should be had to the accompanying drawings and descriptive matter in which there are illustrated and described the preferred embodiments of the invention.

DETAILED DESCRIPTION OF PREFERRED EMBODIMENTS

Figure 1:
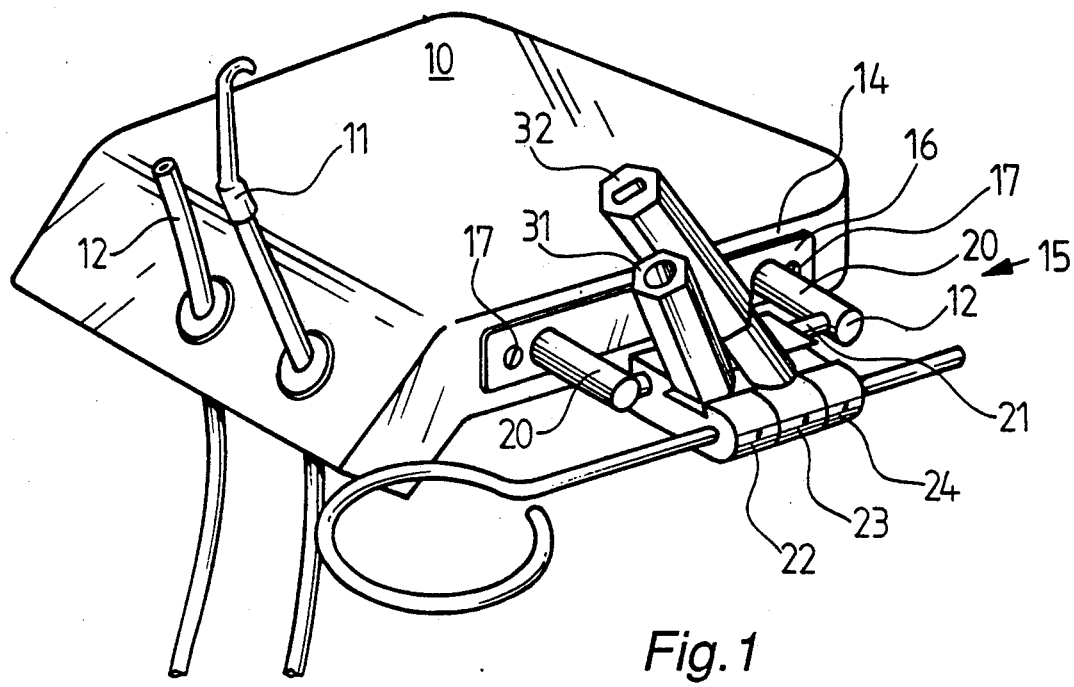
FIG. 1 is a perspective view of a conventional dental instrument panel having mounted on its side one form of mounting support device in accordance with the invention.

FIG. 1 illustrates a typical instrument panel of the type commonly found in dentists' offices. The panel 10 is typically mounted on a floor stand adjacent to the patient's chair, is movable to various positions, and supports a variety of tools 11, 12, only two of which are briefly outlined. Typical tools include a high-speed handpiece, aspirator, air spray, water spray, mirror, etc. The details are unnecessary to the present invention.

In accordance with the invention, a mount 15 for a bracket 12 is secured to the side 14 of the instrument panel 10. The mount 15 comprises a plate 16 screwed 17 to the panel side. Extending from the mount are two posts 20 across which is mounted a support bar 21. The support bar 21 accomodates one or more tool holder supports 22, 23, 24 in accordance with the invention. Some instrument panels made by certain manufacturers come already equipped with a bracket 12 for other purposes. That bracket can be used with the holders of the invention. Otherwise, it is necessary to provide such a bar bracket 12 on the panel.

Figure 3:
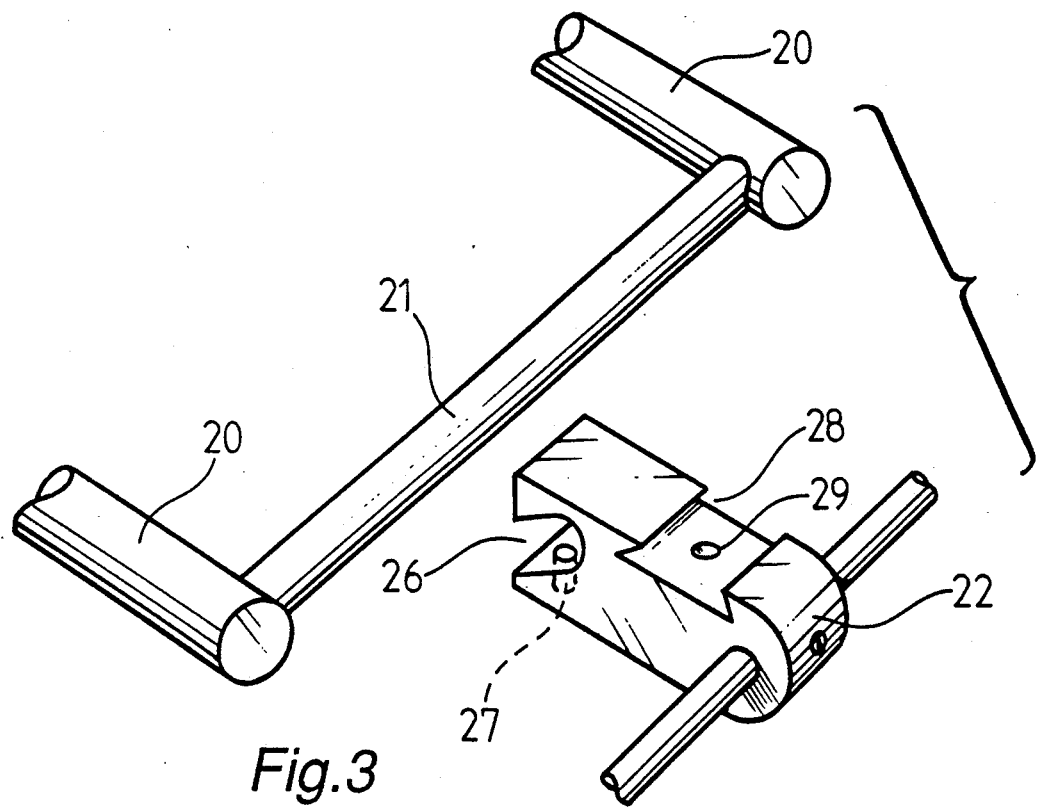
FIG. 3 is an exploded perspective view of the support bracket of the device of FIG. 1 including the grooved tool holder.

FIG. 3 illustrates the mounting means for one of the holder supports 22. The other holder supports would be similar. It comprises a member, preferably of metal, having at one end a generally C-shaped recess or opening 26 sized to fit closely around the bar 21, yet allow sliding movement along the bar. A set screw 27 at the bottom can be used to fix the position of the holder support 22 on the bar 21.

The holder support 22 comprises a dovetail groove 28 which extends across the upper surface of the holder support. A small depression 29 at the groove center is for receiving a ball detent on a tool holder. The tool holder that can be mounted in the groove 28 are of the same basic types discussed in my prior application, Ser. No. 595,238, but they must have a multi-sided or polygonal base configured to slide into the groove 28 in any of several positions so that the tool holder can occupy different orientations for the dentist's convenience.

FIG. 1 illustrates two dental tool holders 31, 32 mounted, respectively, in the aligned grooves 28 of two adjacent support members 22, 23. Alternatively, a single support member can be substituted which is wide enough to hold 2, 3 or more tool holders 31, 32. The tool holder 31 can be, for example, a syringe holder as illustrated in FIG. 8 of application, Ser. No. 595,238, but fitted with a hexagonal base as illustrated in FIG. 10 of that application. The second tool holder 32 can be a scalpel holder of the type illustrated in FIG. 12 of my prior application, again fitted with a hexagonal base. The top half can be separated and removed from the bottom half, so that the used blade can be removed and disposed of allowing the holder to be reused. Or, alternatively, the holder can be provided at the bottom of its hexagonal base with a removable plug to seal off the bottom cavity containing the used blade. Removing the holder and the plug allows disposal of the used blade and re-use of the holder.

Figure 2:
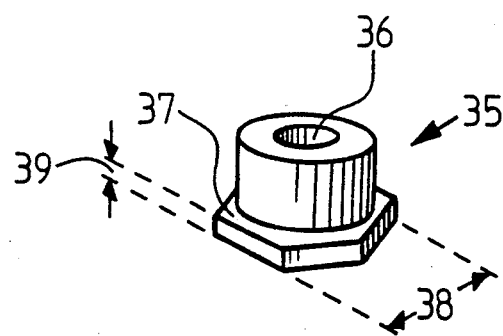
FIG. 2 is a perspective view of one form of crucible in accordance with the invention.

FIG. 2 illustrates another device 35 that can be mounted in the groove 28 of the support 22, 23 or 24. This device 35 is a crucible, used for mixing and holding tooth filling material in a small cup or well 36 at the top. It has a hexagonal base 37 that extends beyond the crucible body, and has a width 38 across its parallel side and a thickness 39 so that the base 37 will slideably fit within the groove 28, with the base 37 lying under the inturned groove edges. Not shown in FIG. 2 is a spring biased ball detent which can be added at the bottom of the base 37 which engages the recess 29 to hold the device 35 in place, even if the instrument panel is moved. The tool holders 31, 32 could have similar means to hold it in position, or rely on friction in the dovetail groove. Since the device 35 is held tightly in place, the user need use only one hand to mix and use the filling material while in the device 35. Other devices such as dappen dishes or the like, capable of holding various items can also be conveniently mounted on the supports 22-24.

Figure 5:
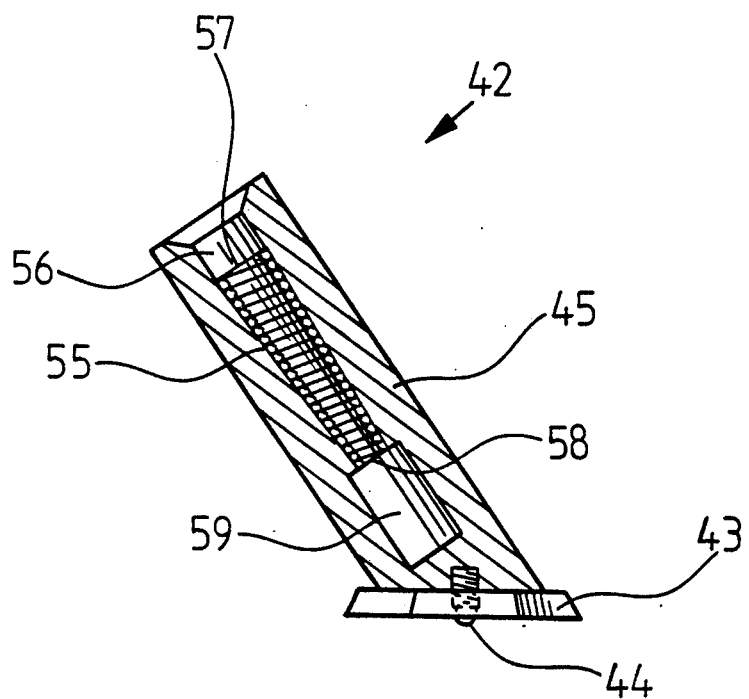
FIG. 5 is an elevational cross-section view of a syringe holder in accordance with the invention.

FIG. 5 illustrates another tool holder 42 with a widened hexagonal base 43 configured to fit the groove 28 of the support 22. A ball detent 44 is shown here at the base bottom. The base 43 is angled relative to the axis of the body 45 of the holder. A suitable angle is 20°-40°. Since the base 43 can slide into the groove 28 in 6 different positions, it means that the body 45 can occupy different orientations relative to the support 22. FIG. 1 shows two of the six possible tool holder orientations.

FIG. 5 also discloses a novel form of safe syringe holder. The typical commercial syringe 50 (FIG. 6) comprises a metal barrel 51 for receiving a cartridge (not shown) storing medication. A narrow end 52 receives the threaded hub of a needle (not shown) which projects forwardly. A plastic protective cover or sleeve 53 is friction-fitted or threaded onto the barrel end 52 over the needle. My earlier filed application shows the typical construction and it need not be repeated here. It need only be mentioned that by grasping the cover 53 and rotating it or the syringe 50 relative to one another, the sleeve 53 can be removed exposing the needle for use. For safety's sake, for the reasons given in my earlier cases, the used needle must be re-covered for safe disposal, preferably without hand-holding the cover 53.

In this aspect of the invention, a tapered, threaded member 55 is mounted about midway within an elongated opening 56 in the holder body 45. The threaded member 55 has a wide end 57 and a narrow end 58 which opens into a cavity 59 at the holder bottom. The member 55 can be a spiral metal spring of the type used in electrical wire nuts. The threads are used to bite into the plastic cover so it will be gripped when the syringe is first inserted in the holder 42 by the dentist. Yet, the syringe can be rotated out of the holder in the same way that wire nuts can be attached and detached from twisted wire ends.

Figure 6:
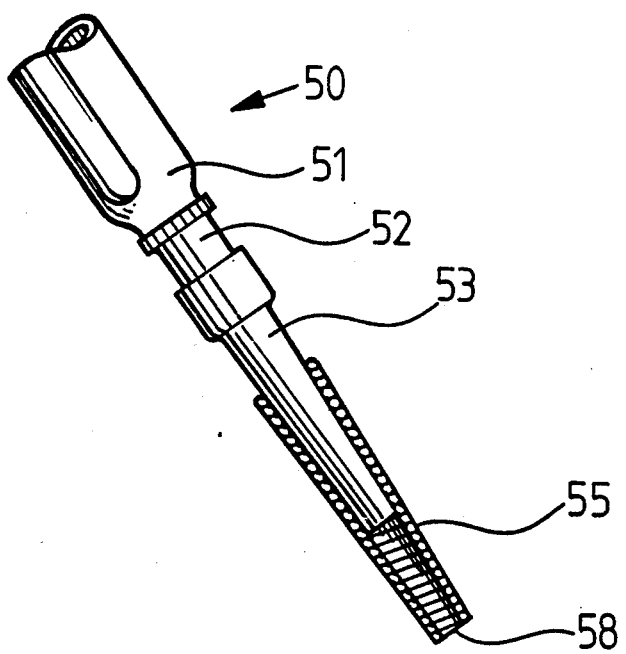
FIG. 6 is a partly cross-sectional view of the tapered threaded member used in the syringe holder of FIG. 5, shown supporting a syringe.

The taper is important to handle the large variety of cover shapes and sizes. I have found that a wide opening 57 of about 0.36 inches, a narrow opening 58 of about 0.15 inches, with an overall length of about 15/16 inches, is sufficient to handle virtually all the conventional sized syringe needle covers. FIG. 6 shows how the spring 55 (the holder 45 is omitted for clarity) can grip the needle cover 53.

In operation, the dentist inserts the syringe with fresh needle and cover into the holder 45, and rotates slightly counter clockwise (ccw) for the threads to grip the cover. Then the dentist can continue to rotate the syringe 50 ccw which will allow it to be removed from the cover 53 which remains behind in the holder 42. The dentist can always place the syringe, with the same patient, back into its held cover 53, and again remove and use. In other words, the needle cover 53 is now functioning as a syringe holder. When the procedure is completed, the dentist reinserts the syringe for the last time into its cover 53, rotates cw to lock the cover 53 to the syringe hub 52, and by continuing cw rotation can now remove the syringe 50 with attached cover 53 from the holder 42. The dentist can now easily and safely remove the used needle protected by the cover 53 for safe disposal. With the holder 42 fixed in place, the entire operation can be performed by the dentist or his assistant using only one hand.

Figure 4:
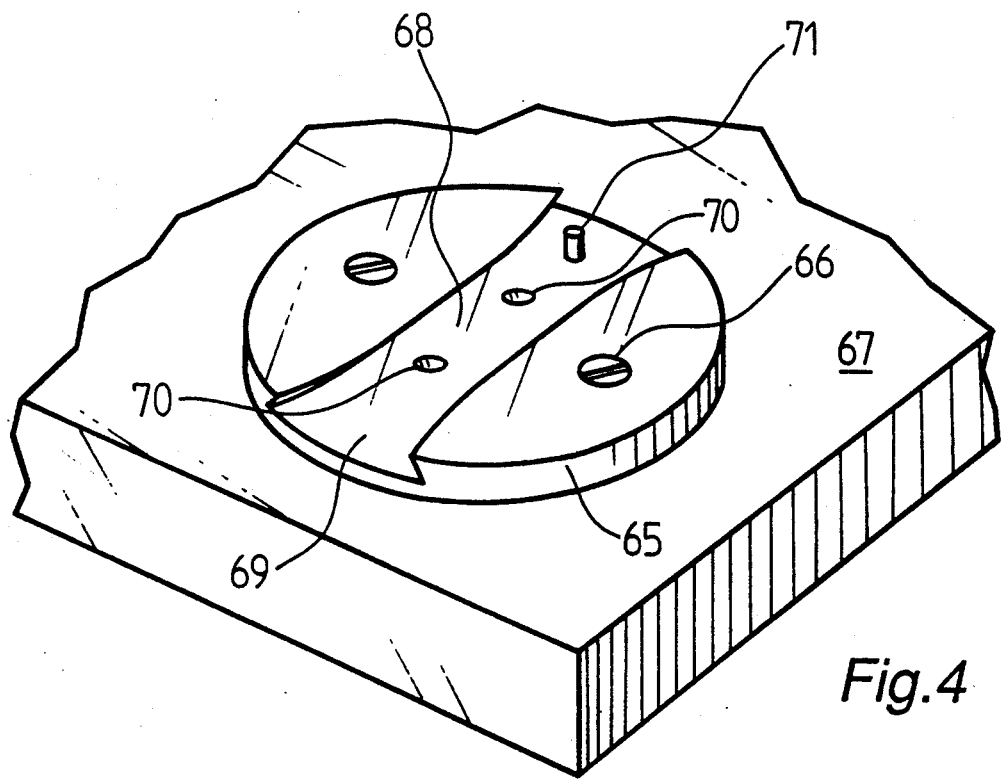
FIG. 4 is a perspective view of a modified tool holder in accordance with the invention for mounting on a work surface.

FIG. 4 illustrates a modified stand for a tool holder of the types disclosed at 31, 32, 35 or 42. It comprises a plate 65 which may be screwed 66 down on a counter top 67 in the dental office. A dovetail groove 68 extends across the top. In this case, the groove ends can be widened 69 for easy attachment and detachment of the holder polygonal base. Two depressions 70 are shown for ball detents so that two tool holders can be slid side-by-side into the groove 68. A stop 71 can be provided if desired for the tool holders.

While the invention has been described in connection with preferred embodiments, it will be understood that modifications thereof within the principles outlined above will be evident to those skilled in the art and thus the invention is not limited to the preferred embodiments but is intended to encompass such modifications.

I claim:

1. A dental tool holder support comprising a support member having a groove across its upper surface for removably receiving a dental tool holder, said groove having along opposed sides undercut edges forming part of a dovetail joint, means along one side of the support member for mounting the support member on a bracket or like support surface, said mounting means comprising an exposed generally C-shaped edge surface configured to embrace a rod on the bracket.

2. A dental tool holder support as claimed in claim 1, further comprising means in the grooved surface for receiving biasing means on the holder.

3. A dental tool holder support as claimed in claim 1, further comprising a hole in the support member extending parallel to the groove.

4. A dental tool holder support as claimed in claim 2, wherein the means for receiving biasing means comprises a depression.

5. In combination: a bracket having a rod for mounting on a dental instrument panel; a support member removably mounted on the bracket rod and having an undercut groove along its upper surface; at least one cup-like dental tool holder having an open top and at its bottom a polygonal base removably mounted in the groove of the support member.

6. The combination of claim 5, wherein the support member has a recessed edge for embracing the bracket rod, and the groove is dovetailed.

7. The combination of claim 5, further comprising a rod slidingly mounted on the support member and having a circular end for receiving a cup.

8. A dental syringe holder comprising an elongated hollow member, means having a tapered threaded opening mounted inside the hollow member with the wide end of the taper facing one end of the hollow member, said hollow member having a polygonal base at its opposite end.

9. The syringe holder of claim 8, wherein the tapered threaded opening comprises a metal spring located about midway in the hollow member.

10. The syringe holder of claim 9 for a syringe, wherein the syringe has a needle, and the tapered threaded opening is sized to grip a removable cover protecting the syringe needle.

11. The syringe holder of claim 9, wherein the polygonal base is hexagonal and is wider than the hollow member and is angled with respect to the hollow member.

12. In combination: a dental syringe holder comprising an elongated hollow member having a bottom and having a tapered threaded top opening with the wide end of the taper adjacent the top end of the hollow member, said hollow member having means for mounting the holder on a support surface; a dental syringe having a removable cover protecting a needle attached to the syringe, said cover having at least at one portion an outer diameter having a size between the inside diameters of the wide and narrow ends of the tapered opening, whereby when said syringe is positioned such that its removable cover is located in the tapered threaded opening of the hollow member, the removable cover can be gripped and held by the threads allowing removal and insertion of the needle, while attached to the syringe, from and into, respectively, its removable cover.

13. The combination of claim 12, wherein the mounting means comprises at the hollow member bottom a hexagonal member angled with respect to the axis of symmetry of the tapered opening.

* * * * *